United States Patent [19]

Miller

[11] Plant 4,023

[45] Mar. 22, 1977

[54] GOLDEN BOSTON FERN

[76] Inventor: Robert O. Miller, P.O. Box 120, Smith River, Calif. 95567

[21] Appl. No.: 665,811

[22] Filed: Mar. 10, 1976

[51] Int. Cl.[2] ..... A01H 9/00

[52] U.S. Cl. ..... Plt./88

[58] Field of Search ..... Plt./88

*Primary Examiner*—Robert E. Bagwill
*Attorney, Agent, or Firm*—James R. Cypher

[57] ABSTRACT

This invention relates to a new and distinct plant which is a sport of *Nephrolepsis exaltata bostoniensis.*

1 Drawing Figure

BACKGROUND OF THE INVENTION

This sport was selected from a large commercial planting of Boston ferns in our greenhouses at Smith River, Calif. because of its distinct golden color. This plant appeared as 11 individual plants from runners on one larger plant and was selected, planted separately, and vegetatively propagated by runners in November, 1973. From the time of selection to the present, a period of 2 years, no further sports of similar nature have appeared in our extensive plantings and no plant propagated from the original Golden Boston ferns have "reverted" to a green Boston Fern.

DESCRIPTION OF THE INVENTION

This plant is free growing, initially erect but with older fronds pendulous. Leaves are pinnately divided with the pinnae articulated, with succulent petioles.

The pinnae are linear-lanceolate, acute, up to 5cm in length and 1cm in width and entire. The frond is more flexible than Boston fern with a waxy feel and appearance. No sori have been observed. In general overall aspects the plant is a Boston fern differing mainly in color.

Color is somewhat variable depending on environmental conditions ranging from Chip 145A to Chip 154B on the Royal Horticulture color chart published by the Royal Horticultural Society, London, 1966. The following table indicates the affect of the environment on color.

| | | |
|---|---|---|
| Very high light (3000 F.C.) | 150B–154B | Yellowest color |
| High light (2000–2500 F.C.) | 145A–145B | Intermediate |
| Low light (1500 and below F.C.) | 144B–144C | Slight greenish appearance |
| High fertility over 85 micromhos (5:1) | | Higher fertility results in greenish appearance |
| Low fertility .30–.85 micromhos (5:1) | | Yellowest color |
| High Temperature (70–80 degrees F) | | Slight greenish appearance |
| Low temperature (below 68 degrees F) | | Yellowest color |

General growth is characteristic of Boston fern except that growth is slower, on the order of 60 percent that of Boston fern. Runners are freely produced in this same relationship.

I claim:

1. A new and distinct variety of Boston fern having the characteristics of Boston fern but differing in that it is yellow to golden color, and has a growth rate approximately 60 percent that of Boston fern.

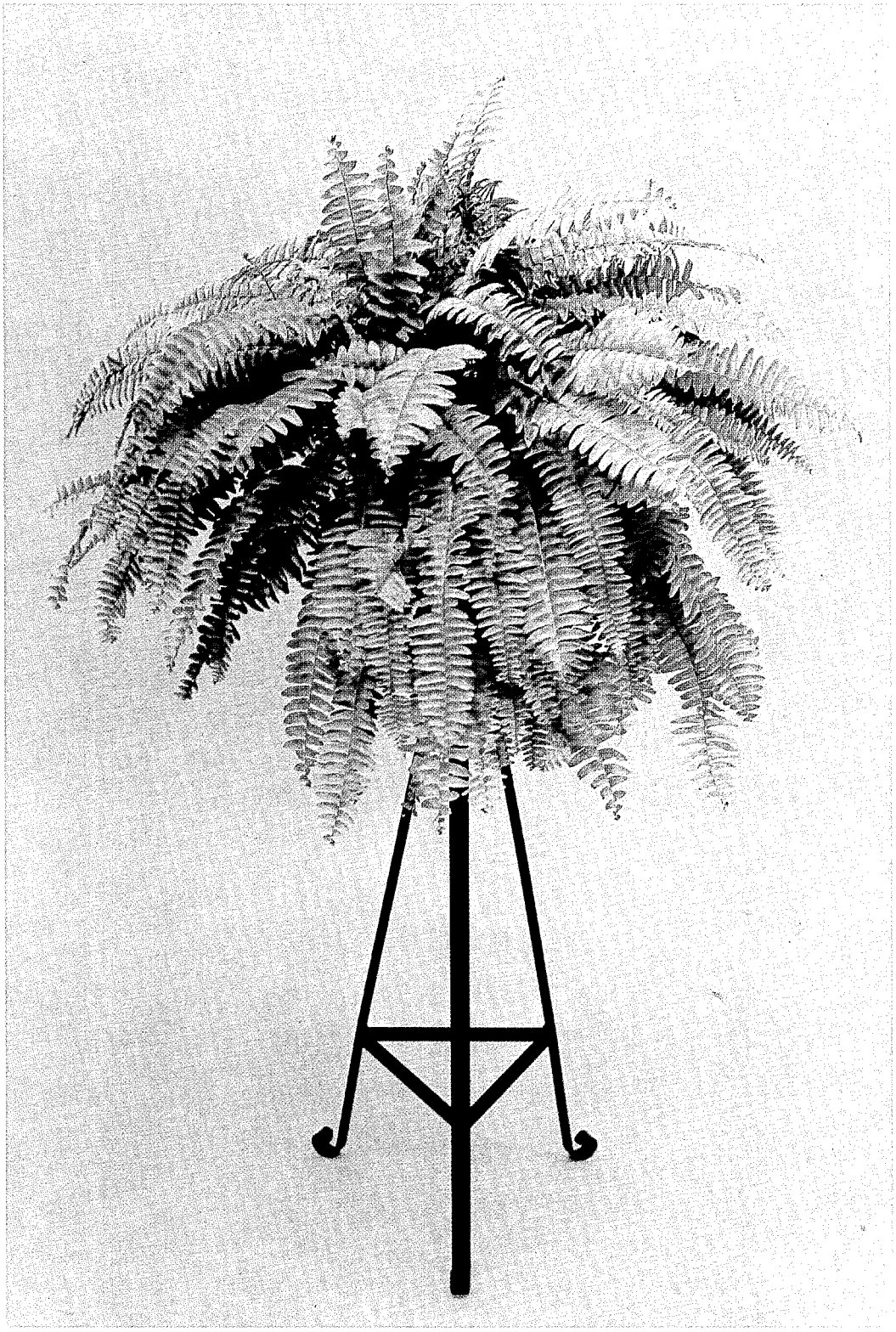

* * * * *